US012262928B2

(12) United States Patent
Deshpande et al.

(10) Patent No.: US 12,262,928 B2
(45) Date of Patent: Apr. 1, 2025

(54) SYSTEM FOR VARYING DISTANCE BETWEEN BONE SEGMENTS

(71) Applicants:Rohan Milind Deshpande, Nagpur (IN); Ayush Sanjay Gaikwad, Chandkapur (IN)

(72) Inventors: Rohan Milind Deshpande, Nagpur (IN); Ayush Sanjay Gaikwad, Chandkapur (IN)

(*) Notice: Subject to any disclaimer, the term of this patent is extended or adjusted under 35 U.S.C. 154(b) by 164 days.

(21) Appl. No.: 18/004,070

(22) PCT Filed: Jun. 30, 2021

(86) PCT No.: PCT/IN2021/050640
§ 371 (c)(1),
(2) Date: Jan. 3, 2023

(87) PCT Pub. No.: WO2022/009219
PCT Pub. Date: Jan. 13, 2022

(65) Prior Publication Data
US 2023/0301691 A1 Sep. 28, 2023

(30) Foreign Application Priority Data
Jul. 7, 2020 (IN) .............................. 202021028776

(51) Int. Cl.
*A61B 17/72* (2006.01)
*A61B 17/86* (2006.01)
(52) U.S. Cl.
CPC ...... *A61B 17/7216* (2013.01); *A61B 17/7233* (2013.01); *A61B 17/863* (2013.01)
(58) Field of Classification Search
CPC ................................................ A61B 17/7216
See application file for complete search history.

(56) References Cited

U.S. PATENT DOCUMENTS 4,931,055 A * 6/1990 Bumpus ............. A61B 17/7014
606/907
11,278,330 B2 * 3/2022 Janda ................. A61B 17/7216
(Continued)

FOREIGN PATENT DOCUMENTS

JP 2019518528 7/2019

OTHER PUBLICATIONS

Horas et al. "A novel intramedullary callus distraction system for the treatment of femoral bone defects," Strategies Trauma Limb Reconstr. Aug. 2016;11(2):113-21. doi: 10.1007/s11751-016-0255-5. Epub May 24, 2016.

*Primary Examiner* — Tessa M Matthews
(74) *Attorney, Agent, or Firm* — JMB Davis Ben-David

(57) ABSTRACT

A system for varying distance between bone segments comprises an intramedullary nail (100) and a driving shaft (210). The intramedullary nail (100) comprises a head (110) attached relative to a first bone segment (410); a housing (120) attached with the head (110); a rotational to linear motion convertor mechanism (140) having an input part and an output part (160); and a transmission (130) having an input member (131) & an output member (133), operatively coupled with input part (150) of rotational to linear motion convertor mechanism (140) and configured to transmit rotational motion and power at an angle. Further, at least a portion of the rotational to linear motion convertor mechanism (140) is contained in the housing (120) and the output part (160) is attached relative to a second bone segment (420). Additionally, the driving shaft (210) is configured to detachably connect with an input member (131) of the transmission.

17 Claims, 11 Drawing Sheets

(56) References Cited

U.S. PATENT DOCUMENTS

| | | |
|---|---|---|
| 2006/0241767 A1 | 10/2006 | Doty |
| 2016/0183994 A1* | 6/2016 | Quach ................ A61B 17/8866 606/90 |
| 2021/0386464 A1* | 12/2021 | Gaudreau ........... A61B 17/8019 |
| 2024/0122632 A1* | 4/2024 | Mei-Dan ............ A61B 17/7241 |

* cited by examiner

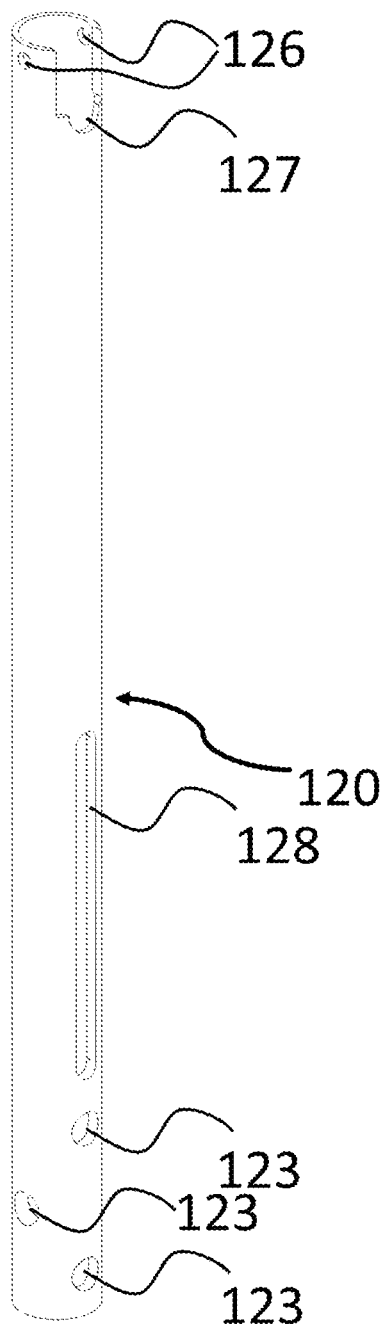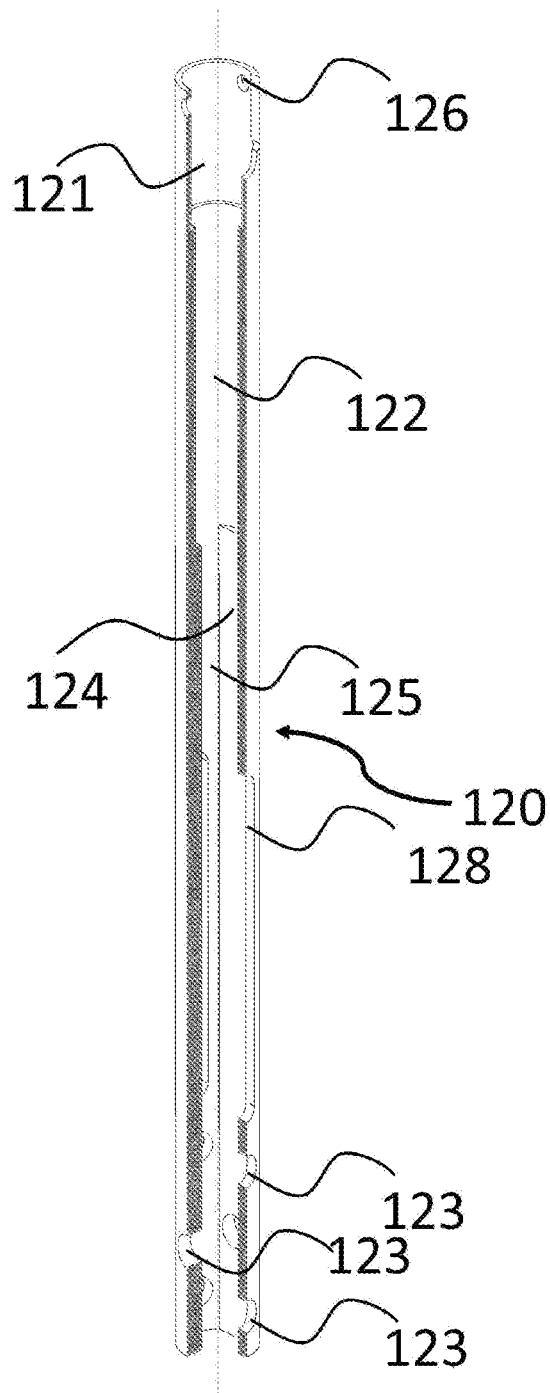
Fig. 17        Fig. 17s

SYSTEM FOR VARYING DISTANCE BETWEEN BONE SEGMENTS

CROSS-REFERENCE TO RELATED APPLICATIONS

This is the U.S. National Stage of International Patent Application No. PCT/IN2021/050640 filed on Jun. 30, 2021, which claims priority to Indian Patent Application No. 202021028776 filed on Jul. 7, 2020.

FIELD OF INVENTION

Present invention in general relates to the field of biomedical engineering and more particularly to a system for varying distance between bone segments.

BACKGROUND OF THE INVENTION

Distraction osteogenesis is a technique used in orthopaedic surgery to repair skeletal deformities, reconstruction surgery and to treat fractures. Limb lengthening surgery is one such technique that is used to lengthen (increase the length) a bone (for example a femur or tibia). The procedure starts with a corticotomy, or osteotomy, of the bone. Which means cutting the bone. The two segments of the bone are distracted (moved) apart from each other at a particular rate. This creates a gap between them. As it's a fracture the body regenerates new bone in the gap. As the gap is increased, new bone keeps filling the gap slowly over time. This technique increases the length of the bone ultimately increasing the length of the limb (as muscles, fascia, veins nerves, etc. all stretches and lengthens in the process). In medical conditions with skeletal defects such as short stature, leg length discrepancy, pseudoarthrosis, bone infection, bone cancer, malunion, nonunion of bone and prior bone fracture did not heal correctly while treating fractures, etc. due to congenital or acquired reasons, can be treated with distraction osteogenesis. Even bone transport surgery is done by distraction osteogenesis. Distraction nails also called distraction rods or distraction implants and external frames called external fixator and ilizarov frames are devices used in the process of distraction osteogenesis for limb lengthening and reconstruction surgeries. These devices are also useful for bone compression. Although various attempts are made for providing various means for osteodistraction and few of them are discussed below.

US 20190133650A1 discloses an intra-corporal telescopic osteodistraction device, an extra-corporal force producing device, a method for bone lengthening and a bone lengthening arrangement. This document talks about an intra-corporal telescopic osteodistraction device for locking the length of the bone and for providing axial, torsional and bending stability; an extra-corporal force producing device, for producing a force for extension causing a lengthening of the intra-corporal device and the bone; a method for bone lengthening and a bone lengthening arrangement utilizing the devices mentioned therein.

WO 2015/184397 AI discloses an extra medullary bone lengthener and use thereof that is an internal device that does not require nailing. This document talks a telescoping plate that attaches to the upper and lower portions of the bone via screws; a small motor affixed on or within the plate. This motor, controlled remotely, will controllably lengthen the bone. The bone will be cut (osteotomy) then the plate will be applied to both ends and fixed to each end with screws. The motor will be controlled from outside by a remote control which will allow the plate to expand causing lengthening of the attached bone.

U.S. Pat. No. 5,415,660A is closes an implantable intramedullary bone lengthening device for correction of limb length deficiencies without a need for transcutaneous connections. The implantable intramedullary bone lengthening nail has an implantable housing, an adjustment mechanism attached to the telescoping cylinder housing, and a drive assembly attached to the housing and the adjustment mechanism for transmitting an expansion force to the adjustment mechanism. The implantable housing may be sealed, encapsulating the unit. The intramedullary bone lengthening nail is inserted into the intramedullary cavity of a bone, which may have been enlarged by reaming. The implantable housing of the intramedullary nail is formed from two telescoping cylinders and is affixed at either end to the bone using pins. The adjustment mechanism is attached to both cylinders of the housing and includes a mechanism for expanding the nail and a ratcheting mechanism for regulating the expansion. The drive assembly includes a shape memory alloy to provide an expansion force. The drive mechanism transmits the expansion force in response to an external signal to the adjustment mechanism.

US 20080039861A1 discloses method and system for facial osteodistraction using a cannulated device. This disclosure provides for a midface distraction system which includes a cannulated distraction rod having a socket disposed adjacent a first end, and a threaded portion disposed between the socket and a second end of the rod. The mid-face distraction system may further include a cannulated malar pin having a flange at a first end and a second end 4 configured to form a moveable coupling between the cannulated malar pin and the socket.

US 20110004246A1 discloses internal osteodistraction device. This document talks an internal osteodistraction device, which includes two fixing points for attachment to a bone in such a way that the distance between the fixing points can be increased in a controlled manner, and a magnetostrictive element which produces a reciprocating mechanical motion in a changing magnetic field. The magnetostrictive element is configured for taking up solely a compressive or tensile force, such that the magnetostrictive element pushes a unidirectional movement permitting element which allows for an increase in the distance between the fixing points, and as the magnetostrictive element is in the process of returning to its original length, a second unidirectional movement permitting element allows the magnetostrictive element to resume its original length without changing a distance between the fixing points of the distraction device.

US 20070010814A1 discloses a device for extending bones, comprising two elements that can be displaced in relation to one another and that are interconnected by at least one drive element. When the two elements are displaced axially in relation to one another, they are guided in a manner that prevents relative radial torsion.

The existing method and devices for osteodistraction suffer various practical shortcomings such as lack of reversibility, lack of strength, lack of distraction force, difficulty in implanting in patients, immobilization of patients, etc. therefore to overcome these problems of the conventional devices and existing arts discussed above and other existing arts, there is need to develop and design an improved and efficient intramedullary nail for use in osteodistraction, bone compression and bone transport.

OBJECT OF THE INVENTION

The primary object of the present invention is to provide a system to distract and/or compress and/or transport bone segment/s.

Another object of the present invention is to vary the distance between the bone segments by varying the distance between the parts of the intramedullary nail which are fixed (in rigid connection) to different bone segments.

Yet another object of the present invention is to provide an externally (out of the body) operable means which when operated will vary the distance between the bone segments fixed (in rigid connection) to the intramedullary nail.

Yet another object of the present invention is the externally (out of the body) operable means which when attached/connected to the intramedullary nail and operated should result in varying (increase or decrease as intended) the distance between the bone segments fixed (in rigid connection) to the intramedullary nail.

Yet another object of the present invention is to maintain the set distance between the bone segments.

Yet another object of the present invention is to resist torsional deformation/deflection between bone segments fixed to the intramedullary nail.

Yet another object of the present invention is to resist its bending.

Other objects, features and advantages will become apparent from detail description and appended claims to those skilled in art.

SUMMARY OF THE INVENTION

The present invention provides a System for varying distance between bone segments. The disclosed system enables efficient cure and/or management of skeletal deformities and/or bone fractures, by bone distraction, bone fracture compression and bone transport.

According to a first aspect of the invention, a system is provided for varying distance between bone segments. The system comprises an intramedullary nail and a driving shaft. The intramedullary nail comprises a head configured to attach relative to a first bone segment; a housing having at least one axial hole at one end and attached with the head and at least one axial hole is non-circular; a rotational to linear motion convertor mechanism, and a transmission configured to transmit rotational motion and power at an angle; wherein output member of the said transmission operatively couples with input part of rotational to linear motion convertor mechanism. Further, at least a portion of the rotational to linear motion convertor mechanism is contained in the housing; and an output part of the rotational to linear motion convertor mechanism is configured to attach relative to a second bone segment directly or indirectly, which is linearly displaceable relative to the housing and the head. Additionally, the driving shaft is configured to detachably connect with an input member of the said transmission.

In accordance with an embodiment of the present invention, the driving shaft upon connection with the input member of the transmission on one end, radially comes out of the intramedullary nail.

In accordance with an embodiment of the present invention, the rotational to linear motion convertor mechanism comprises a power screw as an input part and a slider as the output part.

In accordance with an embodiment of the present invention, the slider is radially non-circular in at least one portion, which interfaces with a non-circular axial hole of the housing, such that the slider and housing do not rotate relative to each other while axial/linear movement between the housing and the slider is allowed.

In accordance with an embodiment of the present invention, the slider has at least one axial hole from one end, with at least one portion of the said hole has internal threads.

In accordance with an embodiment of the present invention, at least a portion of external threads of the power screw and at least a portion of internal threads of slider interface with each other, such that rotation on power screw relative to slider displaces the slider relative to the head and the housing.

In accordance with an embodiment of the present invention, the slider may further comprise at least one bulged out portion radially, which when approaches proximal the seat or abuts the seat, limits the axial/linear displacement of the slider relative to the housing.

In accordance with an embodiment of the present invention, the intramedullary nail may further comprise a distal part configured to be attached with the second bone segment and to rigidly fix with the slider.

In accordance with an embodiment of the present invention, the transmission is configured to do torque multiplication; wherein the rotational motion transmission and the torque multiplication is done in at least one stage.

In accordance with an embodiment of the present invention, the system may further comprise a tube that covers over a portion of the driving shaft radially and secures an attachment of driving shaft with the input member of transmission.

In accordance with an embodiment of the present invention, the housing may further be configured to be attached with a third bone segment and may further have at least one elongated hole on the radial surface.

In accordance with an embodiment of the present invention, the driving shaft may further be configured to attach with a knob or power tool for ease in providing rotation.

According to a second aspect of the present invention, a system is provided for varying distance between bone segments. The system comprises an intramedullary nail configured for implanting in the intramedullary cavity of bone; and a driving shaft. Further, the intramedullary nail comprises a head, transmission and rotational to linear motion convertor mechanism assembled together. Additionally, one end of the driving shaft is configured to operatively couple with an input member of said transmission after successful coupling, other end of the driving shaft is accessible from outside a human body.

In accordance with an embodiment of the present invention, the head attaches relative to a first bone segment.

In accordance with an embodiment of the present invention, the rotational to linear motion convertor mechanism comprises a power screw as an input part and a slider as the output part.

In accordance with an embodiment of the present invention, the output part of the rotational to linear motion convertor mechanism attaches, directly or indirectly, relative to a second bone segment.

In accordance with an embodiment of the present invention, a rotation of the driving shaft when operatively coupled with the input member of the transmission causes linear displacement of the slider relative to the housing and the head.

In accordance with an embodiment of the present invention, a direction of linear displacement of slider relative to the housing and the head is changed by changing a direction of rotation of the input member.

In accordance with an embodiment of the present invention, the driving shaft is decoupleable from the input member of transmission.

BRIEF DESCRIPTION OF DRAWINGS

This invention is described by way of example with reference to the following drawings. These drawings being referred herein are for the purpose of illustrating preferred embodiments of the invention only, and not for the purpose of limiting the same.

FIG. 17 shows a housing 120 of intramedullary nail 100 of the system of FIG. 3 for bone transport, in accordance with an embodiment of the present invention;

FIG. 17s shows the sectional view of the housing 120 of FIG. 17, in accordance with an embodiment of the present invention;

DETAILED DESCRIPTION OF THE DRAWINGS

Figure 1:
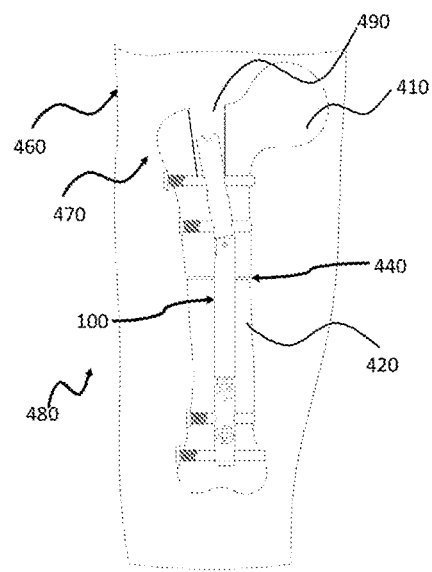
FIG. 1. shows an intramedullary nail 100 of a first embodiment of the system, implanted in an intramedullary cavity 490 of a bone, and is connected with different bone segments 410 and 420.

The present invention is described hereinafter by various embodiments with reference to the accompanying drawings, wherein reference numerals used in the accompanying drawings correspond to the like elements throughout the description. This invention may, however, be embodied in many different forms and should not be construed as limited to the embodiments set forth herein. Rather, the embodiments are provided so that this disclosure will be thorough and complete and will fully convey the scope of the invention to those skilled in the art. In the following description, numeric values and ranges are provided for various aspects of the implementations described. These values and ranges are to be treated as examples only and are not intended to limit the scope of the invention. In addition, a number of materials are identified as suitable for various facets of the implementations. These materials are to be treated as exemplary and are not intended to limit the scope of the invention.

It will be understood by those skilled in the art that the foregoing general description and the following detailed description are exemplary and explanatory of the invention and are not intended to be restrictive thereof.

The terms "comprises", "comprising", or any other variations thereof, are intended to cover a non-exclusive inclusion, Appearances of the phrase "in an embodiment", "in another embodiment" and similar language throughout this specification may, but not necessarily do, all refer to the same embodiment. As used throughout this description, the word "may" is used in a permissive sense (i.e. meaning having the potential to), rather than the mandatory sense, (i.e. meaning must). Further, the words "a" or "an" mean "at least one" and the word "plurality" means "one or more" unless otherwise mentioned. Furthermore, the terminology and phraseology used herein is solely used for descriptive purposes and should not be construed as limiting in scope.

The systems, methods, and examples provided herein are only illustrative and not intended to be limiting.

In simple terms, the present invention can be understood as a system for treating skeletal deformities. An intramedullary nail fixes to a bone segment on one end. A driving shaft connects to an input member of transmission fitted inside the intramedullary nail on one end and comes out of the body on another end. When the driving shaft is rotated (from out of the body), it transmits that motion to the said transmission. The transmission further transmits that motion to a rotational to linear motion convertor mechanism. The linearly displacing part of said rotational to linear motion convertor mechanism is fixed (in rigid connection) with another bone segment (directly or indirectly). When the linearly displacing part displaces, the bone segment fixed (in rigid connection) to it also displaces, resulting in varying the distance between the bone segments. The resultant displacement between bone segments is prismatic and has only one degree of freedom. The intramedullary nail may be fixed (in rigid connection) to two or more than two bone segments. The present invention will now be explained with reference to the drawings:

A system is provided for a varying distance between bone segments, in accordance with the embodiments of the present invention. The proposed invention provides a system that is for varying distance between bone segments by increasing or decreasing the distance between the parts of a system that are fixed (in rigid connection) with different bone segments (directly or indirectly). The system comprises an intramedullary nail, a driving shaft and a tube.

Figure 2:
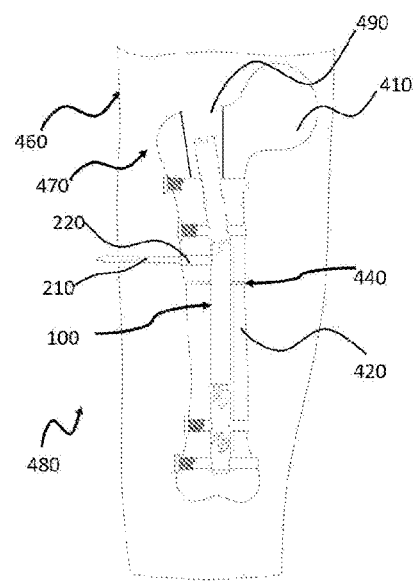
FIG. 2 shows the intramedullary nail 100 of FIG. 1 further connected with a driving shaft 210 and a tube 220, in accordance with an embodiment of the present invention.
Figure 3:
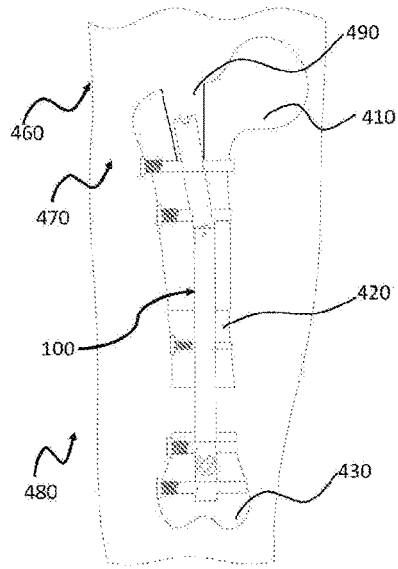
FIG. 3 shows the intramedullary nail 100 of a second embodiment of the system, which is implanted in the intramedullary cavity 490 of the bone, and is connected with the different bone segments 410, 420, and 430.
Figure 4:
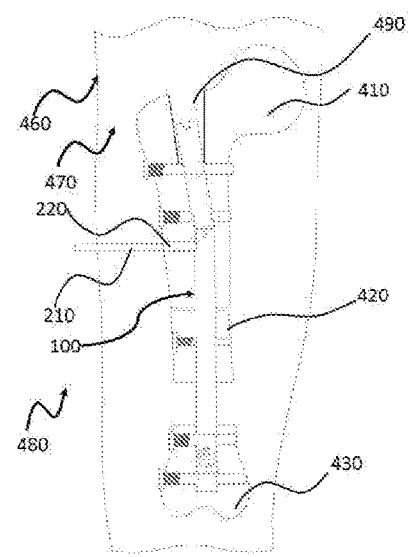
FIG. 4 shows the intramedullary nail 100 of FIG. 3 further connected with the driving shaft 210 and the tube 220, in accordance with an embodiment of the present invention.

FIG. 1 shows the intramedullary nail 100 of a first embodiment of the system, implanted in an intramedullary cavity 490 of a bone, and is configured to attach with different bone segments i.e., a first bone segment 410, a second bone segment 420. Further, FIG. 2 shows the first embodiment of the system, where the intramedullary nail 100 is further connected with the driving shaft 210 and the tube 220. And, FIG. 3 shows the intramedullary nail 100 of a second embodiment of the system, which is implanted in the intramedullary cavity 490 of the bone, and is connected with the different bone segments 410, 420 and 430. Furthermore, FIG. 4 shows the second embodiment of the system, wherein the Intramedullary nail 100 is further connected with the driving shaft 210 and the tube 220.

In accordance with the embodiments of the present invention, the intramedullary nail 100 comprises: a head 110, a housing 120, a transmission 130, and rotational to linear motion convertor mechanism 140. In accordance with an embodiment of the present invention, the intramedullary nail 100 further comprises a distal part 170. The rotational to linear converter mechanism 140 preferably comprise a power screw 150 and a slider 160.

Figure 5:
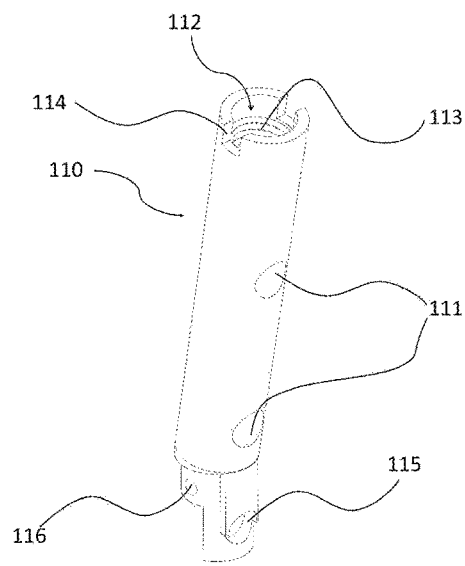
FIG. 5 shows a head 110 of the intramedullary nail 100, in accordance with the embodiments of the present invention.

Additionally, FIG. 5 illustrates the head 110 which is configured to attach with the first bone segment 410 via bone screws 310, through screw holes 111. The head 110 further includes a hole 115 which allows access to input member 131 of transmission 130, another hole 116 to rigidly fix with the housing, a bore 112 with internal threads 113 to connect with a jig and also jig aligners 114.

Figure 6:
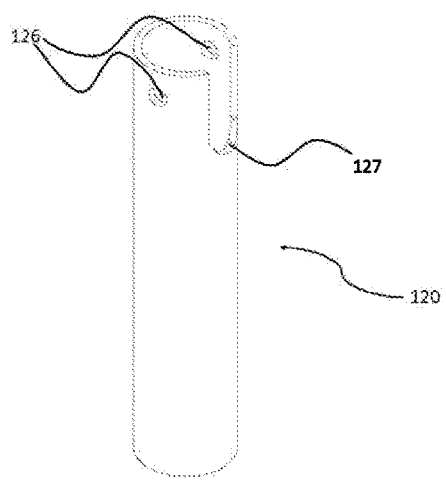
FIG. 6 shows a housing 120 of intramedullary nail 100 of the system of FIG. 1 for limb lengthening and bone compression, in accordance with an embodiment of the present invention.
Figure 6S:
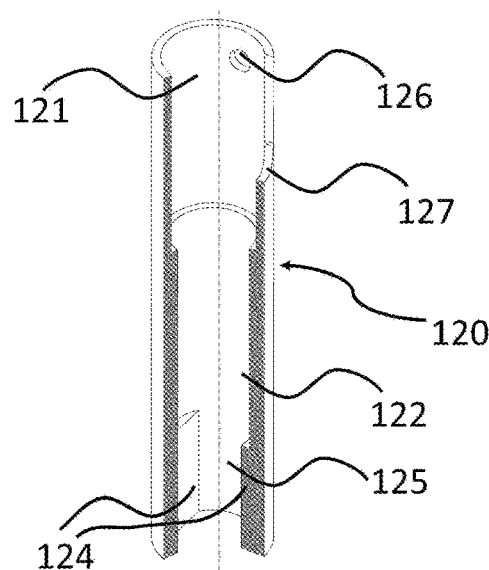
FIG. 6s shows the sectional view of the housing 120 of FIG. 6, in accordance with an embodiment of the present invention.
Figure 7R:
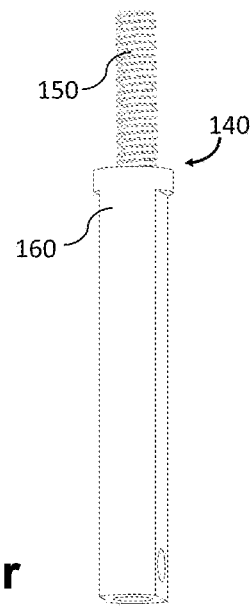
FIG. 7r shows a rotational to linear motion convertor mechanism 140 of intramedullary nail 100, in accordance with the embodiments of the present invention.

Next FIG. 6 shows the housing 120 of first embodiment of the system of—FIG. 1. The housing 120 is a tubular part with an axial hole 122, in which a slider 160 is linearly displaces. The housing 120 has one more axial hole 121 (preferably bigger than the axial hole 122) to fit transmission 130. The housing 120 has a seat 124 to make the axial hole 125 smaller than the axial hole 122 wherein, the seat 124 is configured to restrict/limit the linear displacement of the slider 160 relative to housing 120 as discussed. The shape of at least one of the axial holes 121, 122, 125 of the housing 120 is non-circular. In addition, FIG. 6s shows the housing 120 of the first embodiment of system for limb lengthening and bone compression, wherein the axial hole 125 is non-circular. The housing 120 has one hole 127 radially, for accessing the input member 131 of transmission 130. The housing 120 also has a hole 126 for fastening the housing 120 with the head 110.

Figure 7:
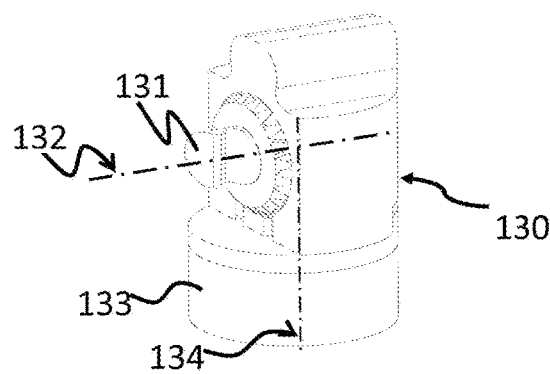
FIG. 7 shows a transmission 130 of intramedullary nail 100, in accordance with the embodiments of the present invention.

Then, FIG. 7 shows transmission 130 where 131 is input member of transmission 130 and 133 is output member of transmission 130. The input member 131 of transmission 130 when provided with rotational motion results in rotation of output member 133 of transmission 130, wherein axis of rotation of input member of transmission 132 and axis of rotation of output member of transmission 134 are inclined to each other. Preferably the angle between the said axes are between 1 to 179 degree and/or 181 to 359 degree. The transmission 130 is preferably designed to multiply torque.

Figure 8:
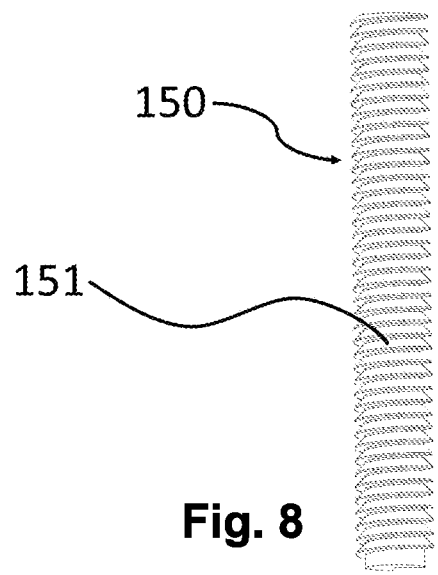
FIG. 8 shows a power screw 150 of the intramedullary nail 100, in accordance with the embodiments of the present invention.
Figure 9:
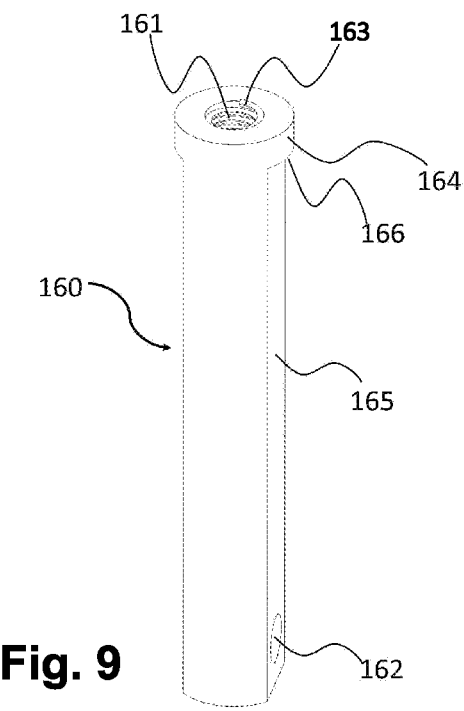
FIG. 9 shows a slider 160 of the intramedullary nail 100, in accordance with the embodiments of the present invention.
Figure 9S:
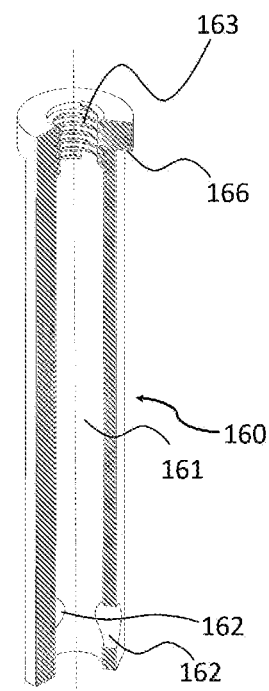
FIG. 9s shows a sectional view of the slider 160 of FIG. 9, in accordance with the embodiments of the present invention.

Further, FIG. 8 shows a power screw 150 which is a rotating part and an input side of the rotational motion to linear motion convertor mechanism 140. External threads of power screw 151 are preferably buttress, or trapezoidal, or acme or square. Also, FIG. 9 shows a slider 160 which is an output part (i.e., a linearly displacing part) of the rotational to linear motion convertor mechanism 140. The slider 160 is configured with bone screw holes 162 to fix with the second bone segment 420 via the bone screws 320. The slider 160 has an axial hole 161, with internal threads 163 in a portion (as in a nut). The threads 163 are preferably buttress, or trapezoidal, or acme or square. At least a portion of slider 160 linearly displaces/slides in the axial hole 122 of housing 120. A portion of slider 165 is non-circular radially. Preferably the non-circular shape has flat and/or convex walls. Then FIG. 9s shows the sectional view of the slider 160 with a bulged out portion 166 radially, which limits the axial/linear displacement of it relative to the housing 120 when the slider 160 is near the seat 124 or abuts the seat 124.

Figure 10:
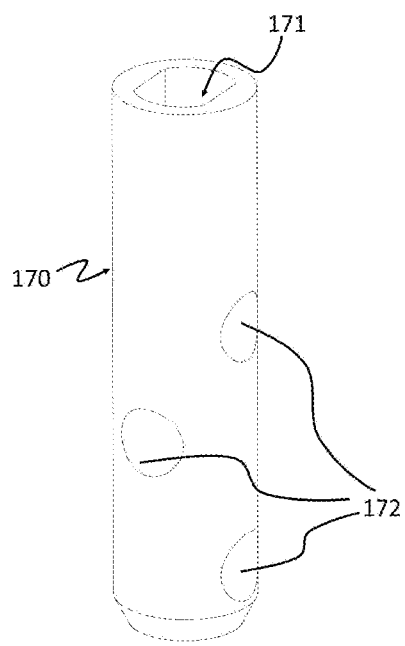
FIG. 10 shows a distal part 170 of the intramedullary nail 100, in accordance with an embodiment of the present invention.
Figure 11:
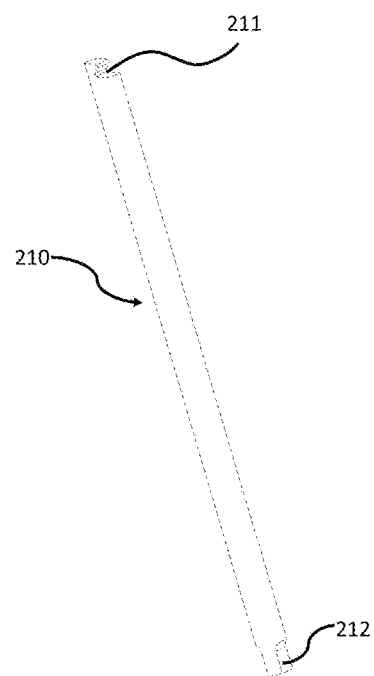
FIG. 11 shows a driving shaft 210 of the system, in accordance with the embodiments of the present invention.

After that, the FIG. 10 illustrates a distal part 170 which is configured to fix with slider 160 and also configured to fix with the second bone segment 420 by bone screw(s) 320 passing through bone screw hole(s) 172. The distal part 170 increases stability of the slider 160 when in the intramedullary cavity of bone 490. Further, FIG. 11 shows the driving shaft 210 whose one end 211 is configured to operatively couple with input member 131 of transmission preferably by attachment/connection and its other end 212 is configured for ease in gripping for rotation.

Figure 12:
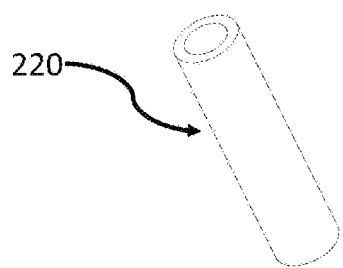
FIG. 12 shows a tube 220 of the system, in accordance with the embodiments of the present invention.

FIG. 12 shows the tube 220, in accordance with the embodiments of the present invention. The tube 220 when covers over the end 211 of the driving shaft 210 which connects/attaches with input member 131 of transmission 130, such that it's covering secures the said connection/attachment from decoupling by axial pull out, prevents osseointegration over the driving shaft 210 and also supports driving shaft 210. When the tube 220 is employed, its length only allows it to come up to or somewhat out of bone 410 and not out of skin 460.

Figure 13:
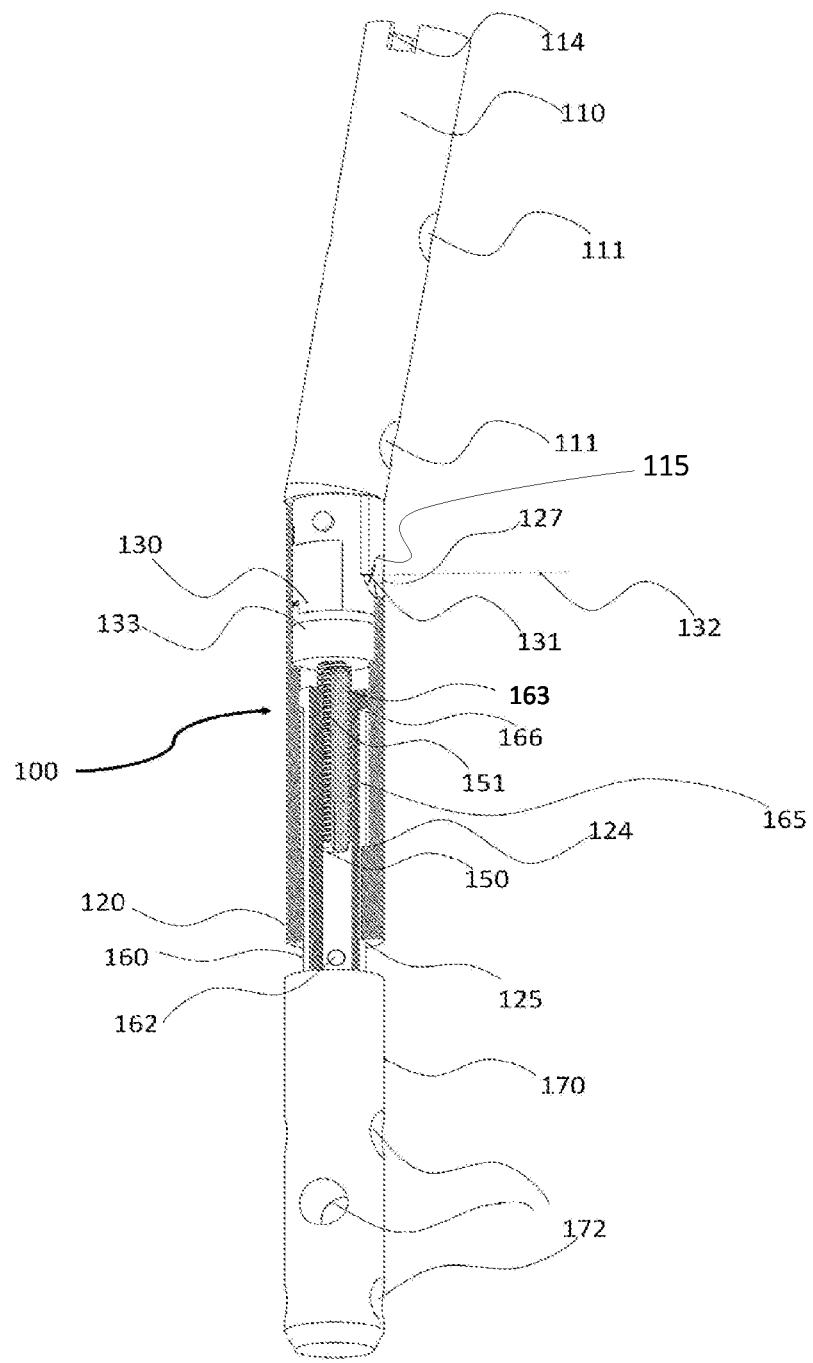
FIG. 13 shows the intramedullary nail 100 of the system of FIG. 1 with sectional view of housing 120, slider 160 and power screw 150.

FIG. 13 shows a complete construction of the intramedullary nail 100 of the first embodiment of the system for limb lengthening and bone compression with sectional view of the housing 120, the slider 160 and the power screw 150. The head 110 is rigidly fixed with the housing 120. The transmission 130 is accommodated between head 110 and housing 120, where the input member 131 of transmission 130 is accessible from opening 127 and 115, and output member 133 of transmission 130 is operatively coupled with power screw 150. The input member 131 of transmission 130 is configured to attach with driving shaft 210 for operative coupling. The power screw 150 is further in the threaded connection with slider 160 (external threads 151 of power screw interface with internal threads 163 of slider). The radially non-circular portion 165 of slider interfaces with non-circular axial hole 125 of housing, such that slider 160 cannot rotate relative to housing 120. The slider 160 is fixed with the distal part 170.

Figure 14:
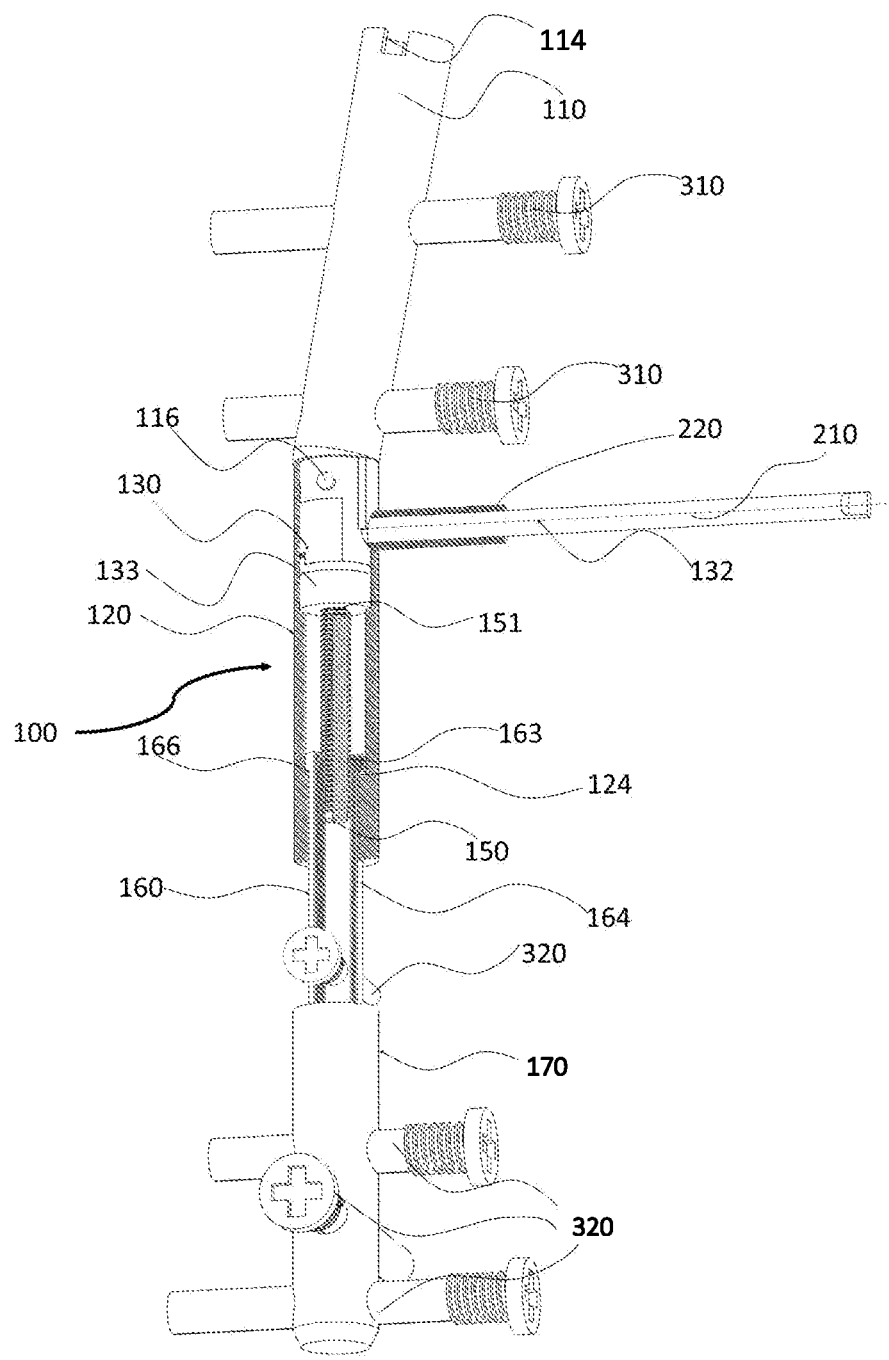
FIG. 14 shows displaced slider 160 of the system of FIG. 2, in accordance with an embodiment of the present invention.

Also, FIG. 14 shows displaced slider 160 of the first embodiment of system, wherein the driving shaft 210 is attached with the input member 131 of transmission 130, and tube 220 is slid over driving shaft 210. When driving shaft 210 is rotated, it transmits motion and power to the input member 131 of transmission 130, the transmission 130 transmits the rotational motion and power at an angle and multiplies the torque and gives rotational motion and power at the output member 133 of transmission 130. This output member 133 of transmission 130 rotates power screw 150 as being operatively coupled with it. The power screw 150 being in threaded connection with slider 160 (as external threads 151 of power screw interface with internal threads of slider 163) and slider 160 not being able to rotate relative to the housing 120, the slider 160 gets linearly displaced relative to the housing 120. The distal part 170 also displaces relative to the head 110 and housing 120.

Figure 15:
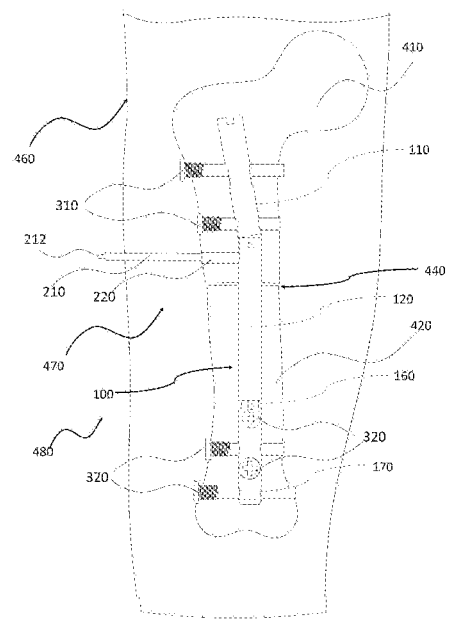
FIG. 15 shows the implanted first embodiment of the system of FIG. 2, in accordance with an embodiment of the present invention.

FIG. 15 shows the first embodiment of system for bone compression and limb lengthening where the head 110 of intramedullary nail 100 is fixed to the first bone segment 410 by bone screws 310, and the slider 160 and the distal part 170 both connect to the second bone segment 420 via bone screws 320. The driving shaft 210 is operatively coupled with the input member 131 of transmission 130 by attachment/connection. The tube 220 is slid over the driving shaft 210 to secure its connection with input member 131 of transmission 130. When the driving shaft 210 is operatively coupled by a physical connection to the input member 131 of transmission 130 it radially comes out of intramedullary nail 100 and it's other end 212 is accessible from out of the body 480.

Figure 15G:
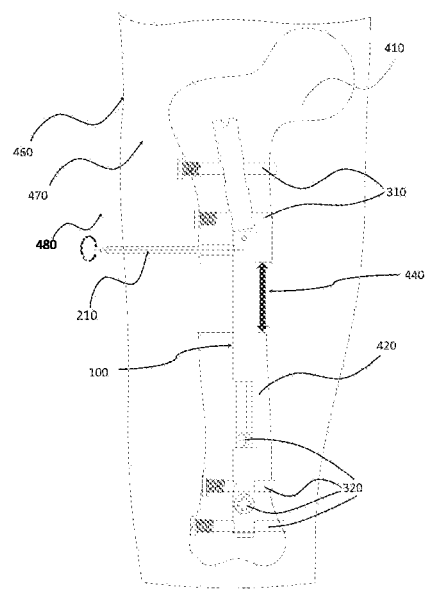
FIG. 15g shows a bone segment gap variation done by the first embodiment of the system of FIG. 15, in accordance with an embodiment of the present invention.

FIG. 15g shows the bone gap 440 variation done by the first embodiment of the system of FIG. 15, by rotating the driving shaft 210 when operatively coupled with input member 131 of transmission 130. By changing the direction of rotation of input member 131 of transmission 130 by changing direction of rotation of driving shaft 210 the direction of linear displacement of slider 160 relative to housing 120 (ultimately distal part 170 and the second bone segment 420) can be changed. The driving shaft 210 can be detached (along with tube 220) from the intramedullary nail 100. The intramedullary nail 100 is preferably kept inside the body 470 until the newly generated bone consolidates and can be removed later.

Figure 16:
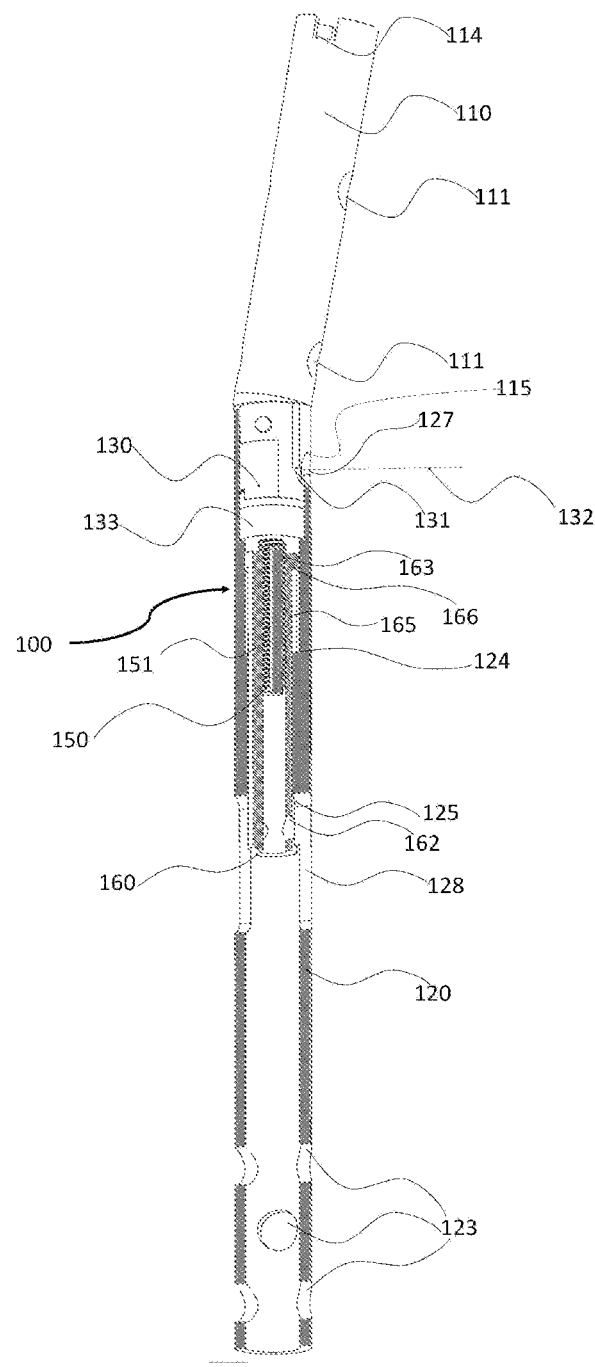
FIG. 16 shows a construction of the intramedullary nail 100 of the system of FIG. 3 for bone transport, with sectional view of housing 120, slider 160 and power screw 150, in accordance with an embodiment of the present invention.

Additionally, FIG. 16 shows the second embodiment of the system for bone transport. The second embodiment uses similar parts, with similar construction and working to the first embodiment with some design variations in a few parts and its fixation with bone segments. These variations are discussed below. FIG. 16 also shows the complete construction of the second embodiment of nail with sectional view of housing 120, slider 160 and power screw 150. The head 110 is rigidly fixed with the housing 120. The transmission 130 is accommodated between head 110 and housing 120, where the input member 131 of transmission 130 is accessible from opening 127 and 115, and output member 133 of transmission 130 is operatively coupled with power screw 150. The input member 131 of transmission 130 is configured to attach with driving shaft 210 for operative coupling. The power screw 150 is further in the threaded connection with slider 160 (external threads of power screw 151 interface with internal threads 163 of slider). The non-circular portion of slider 165 interfaces with non-circular axial hole 125 of housing 120, such that slider 160 cannot rotate relative to housing 120.

FIG. 17 shows the housing 120 of the second embodiment. The housing 120 is similar to the first embodiment with few modifications like extended length, bone screw hole(s) 123 radially, working as configuration to connect to the third bone segment 430 via bone screws 330, and elongated holes 128 which allows establishing connection between slider 160 and second bone segment 420. The elongated holes 128 also allow linear displacement of slider 160 and second bone segment 420 when connected together with bone screw 320.

Figure 18:
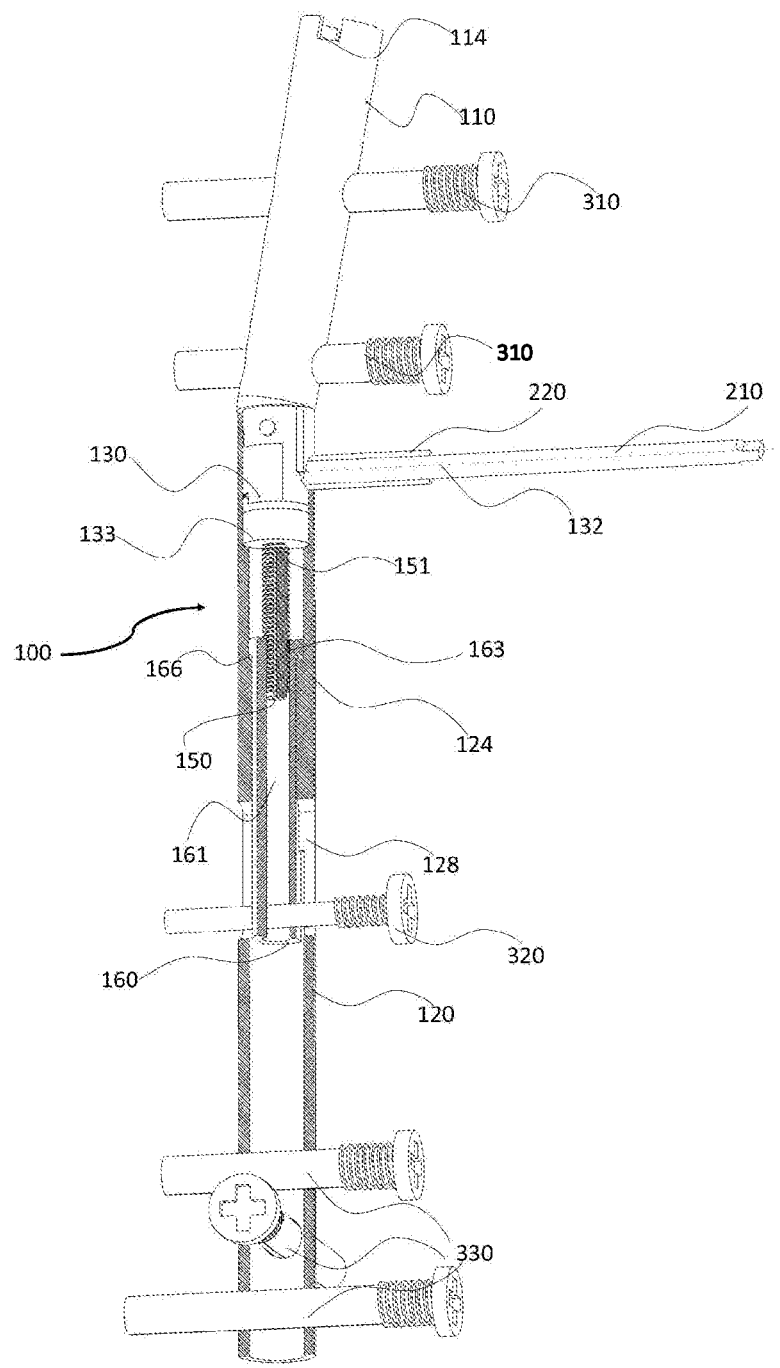
FIG. 18 shows displaced slider of the system of FIG. 4, in accordance with an embodiment of the present invention.

FIG. 18 shows displaced slider 160 of second embodiment of system, wherein the driving shaft 210 is attached with the input member 131 of transmission 130, and tube 220 is slid over driving shaft 210. When driving shaft 210 is rotated, it transmits motion and power to the input member 131 of transmission 130, the transmission 130 transmits the rotational motion and power at an angle and multiplies the torque and gives rotational motion and power at the output member 133 of transmission 130. This output member 133 of transmission 130 rotates power screw 150 as being operatively coupled with it. The power screw 150 being in threaded connection with slider 160 (as external threads 151 of power screw interface with internal threads 163 of slider) and slider 160 not being able to rotate relative to the housing 120, the slider 160 gets linearly displaced relative to the housing 120.

Figure 19:
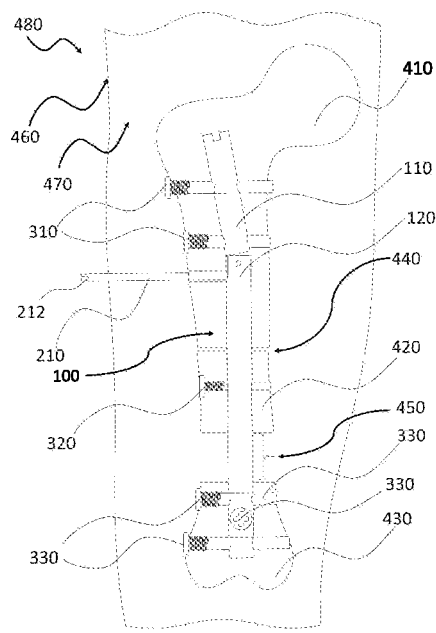
FIG. 19 shows the implanted second embodiment of the system of FIG. 4, in accordance with an embodiment of the present invention.

FIG. 19 shows the second embodiment of system for bone transport where the head 110 of intramedullary nail 100 is fixed to the first bone segment 410 by bone screws 310, the housing 120 is fixed with the third bone segment 430 by bone screws 330, and the slider 160 is fixed the second bone segment 420 via bone screws 320, wherein constant distance is maintained between first bone segment 410 and the third bone segment 430. The driving shaft 210 is operatively coupled with the input member 131 of transmission 130 by attachment/connection. The tube 220 is slid over the driving shaft 210 to secure its connection with input member 131 of transmission 130. When the driving shaft 210 is operatively coupled by a physical connection to the input member 131 of transmission 130 the other end 212 of it is accessible from out of the body 480.

Figure 19G:
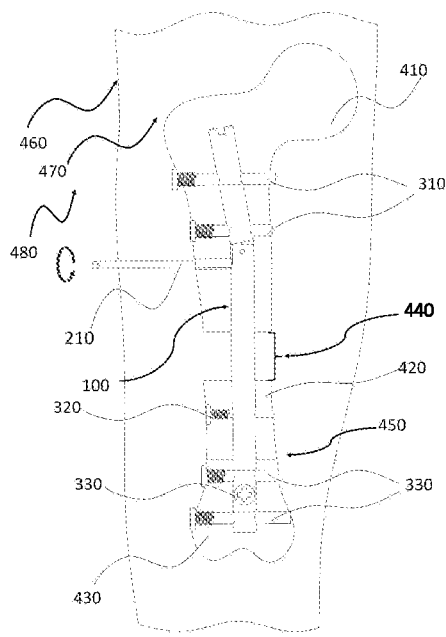
FIG. 19g shows the bone segment gap variation done by the second embodiment of the system of FIG. 19, in accordance with an embodiment of the present invention.

FIG. 19g shows a bone gap 440 and 450 variation done by the second embodiment of the system, by rotating the driving shaft 210 when operatively coupled with input member 131 of transmission 130. By changing the direction of rotation of input member 131 of transmission 130 by changing direction of rotation of driving shaft 210 the direction of linear displacement of slider 160 relative to housing 120 (ultimately the second bone segment 420) can be changed. The driving shaft 210 can be detached (along with tube 220) from the intramedullary nail 100 when required. The intramedullary nail 100 is preferably kept inside the body 470 until the newly generated bone consolidates and can be removed later.

For ease in rotating the driving shaft 210 of the system a part or device can be provided, which is attached to the end of shaft 212. The intramedullary nail 100 of the system is preferably implanted in the intramedullary cavity 490 of bone like tibia, femur, humerus, ulna, and radius. Fracture management by bone compression can be done with the system by decreasing the distance/gap between bone segments.

The foregoing description describes two embodiments of the present invention. It should be appreciated that these embodiments are described for the purpose of illustration only, and that numerous alterations and modifications may be practiced by those skilled in the art without departing from the spirit and scope of the invention. It is intended that

LIST OF REFERENCE NUMERALS:

| No. | Denotes |
|---|---|
| 100 | Intramedullary nail |
| 110 | Head |
| 111 | Bone screw hole to connect with first bone segment |
| 112 | Bore |
| 113 | Threads to attach with Jig |
| 114 | Jig aligner |
| 115 | Transmission access hole on head |
| 116 | Hole for fastening |
| 120 | Housing |
| 121 | Axial hole for transmission |
| 122 | Axial hole for slider |
| 123 | Bone screw hole to connect with third bone segment |
| 124 | Seat |
| 125 | Non-circular hole |
| 126 | Hole for fastening |
| 127 | Transmission access hole on housing |
| 128 | Elongated hole |
| 130 | Transmission |
| 131 | Input member (of transmission) |
| 132 | Axis of rotation of input member (of transmission) |
| 133 | Output member (of transmission) |
| 134 | Axis of rotation of output member (of transmission) |
| 140 | Rotational to linear motion convertor mechanism |
| 150 | Power screw |
| 151 | External threads |
| 160 | Slider |
| 161 | Axial hole of slider |
| 162 | Bone screw hole to connect with second bone segment |
| 163 | Internal threads |
| 164 | Radial surface |
| 165 | Radially non-circular portion |
| 166 | Bulged out portion |
| 170 | Distal part |
| 171 | Configuration to connect with slider |
| 172 | Bone screw hole to connect with second bone segment |
| 210 | Driving shaft |
| 211 | Configuration for attachment with input member of transmission |
| 212 | Driving end (of driving shaft) |
| 220 | Tube |
| 310 | Bone screw for first bone segment connection |
| 320 | Bone screw for second bone segment connection |
| 330 | Bone screw for third bone segment connection |
| 410 | First bone segment |
| 420 | Second bone segment |
| 430 | Third bone segment |
| 440 | Bone gap between first and second bone segment |
| 450 | Bone gap between third and second bone segment |

-continued

LIST OF REFERENCE NUMERALS:

| No. | Denotes |
|---|---|
| 460 | Skin |
| 470 | Region Inside Body |
| 480 | Region outside Body |
| 490 | Intramedullary cavity |

We claim:

1. A system for varying distance between bone segments comprises an intramedullary nail (100) and a driving shaft (210);
   wherein the intramedullary nail (100) comprises:
   a. a head (110) configured to attach relative to a first bone segment (410); characterized in that
   b. a housing (120) having at least one axial hole at one end wherein the at least one axial hole is non-circular (125), and said housing is attached with the head (110);
   c. a rotational to linear motion convertor mechanism (140), wherein at least a portion of the rotational to linear motion convertor mechanism (140) is contained in the housing (120); and wherein an output part (160) of the rotational to linear motion convertor mechanism (140) is configured to attach relative to a second bone segment (420) directly or indirectly and is linearly displaceable relative to the housing (120) and the head (110); and
   d. a transmission (130) configured to transmit rotational motion and power at an angle; wherein an output member (133) of the said transmission (130) operatively couples with an input part (150) of the rotational to linear motion convertor mechanism (140);
   wherein the driving shaft (210) is configured to detachably connect with an input member (131) of the said transmission (130),
   wherein the driving shaft (210) upon connection with the input member (131) of the transmission (130) on one end (211), radially comes out of the intramedullary nail (100).

2. The system as claimed in claim 1, wherein the rotational to linear motion convertor mechanism (140) comprises a power screw (150) as an input part and a slider (160) as the output part.

3. The system as claimed in claim 2, wherein the slider (160) is radially non-circular in at least one portion (165), which interfaces with the non-circular axial hole of the housing (125), such that the slider (160) and the housing (120) do not rotate relative to each other while axial/linear movement between the housing (120) and the slider (160) is allowed.

4. The system as claimed in claim 3, wherein the slider (160) has at least one axial hole (161), with at least one portion of the said hole has internal threads (163).

5. The system as claimed in claim 2, wherein at least a portion of external threads (151) of the power screw (150) and at least a portion of internal threads (163) of the slider (160) interface with each other, such that rotation of the power screw (150) relative to the slider (160) displaces the slider (160) relative to the head (110) and the housing (120).

6. The system as claimed in claim 2, wherein the slider (160) [may] further comprises at least one bulged out portion radially (166), which when approaches proximal a seat (124) or abuts a seat (124), limits the axial/linear displacement of the slider (160) relative to the housing (120).

7. The system as claimed in claim 1, wherein the intramedullary nail (100) further comprises a distal part (170) configured to be attached with the second bone segment (420) and to rigidly fix with the slider (160).

8. The system as claimed in claim 1, wherein the transmission (130) is configured to do torque multiplication; wherein the rotational motion transmission and the torque multiplication is done in at least one stage.

9. The system as claimed in claim 1, further comprises a tube (220) that covers over a portion of the driving shaft (210) radially and secures an attachment of the driving shaft (210) with the input member (131) of the transmission (130).

10. The system as claimed in claim 1, wherein the housing (120) is further configured to attach with a third bone segment (430) and has at least one elongated hole (128) on the radial surface.

11. The system as claimed in claim 1, wherein the driving shaft (210) is further configured to attach with a knob or power tool for ease in providing rotation.

12. A system for varying distance between bone segments comprises:
an intramedullary nail (100) configured for implanting in the intramedullary cavity (490) of a bone; and
a driving shaft (210);
characterized in that
wherein the intramedullary nail (100) comprises a head (110), a housing (120), a transmission (130) and a rotational to linear motion convertor mechanism (140) assembled together;
wherein one end (211) of the driving shaft (210) is configured to operatively couple with an input member (131) of said transmission (130) after successful coupling, other end (212) of the driving shaft (210) is accessible from outside a human/animal body (480), wherein a rotation of the driving shaft (210) when operatively coupled with the input member (131) of the transmission (130) causes linear displacement of a slider (160) relative to the housing (120) and the head (110).

13. The system as claimed of claim 12, wherein the head (110) is configured to attach relative to a first bone segment (410).

14. The system as claimed in claim 12, wherein the rotational to linear motion convertor mechanism (140) comprises a power screw (150) as an input part and the slider (160) as an output part.

15. The system as claimed in claim 14, wherein the output part (160) of the rotational to linear motion convertor mechanism (140) attaches, directly or indirectly, relative to a second bone segment (420).

16. The system as claimed in claim 12, wherein a direction of linear displacement of the slider (160) relative to the housing (120) and the head (110) is changed by changing a direction of rotation of the input member (131) of the transmission (130).

17. The system as claimed in claim 12, wherein the driving shaft (210) is decoupleable from the input member (131) of the transmission (130).

* * * * *